US00PP30120P2

(12) United States Plant Patent
Carruth

(10) Patent No.: US PP30,120 P2
(45) Date of Patent: Jan. 22, 2019

(54) FLORIBUNDA ROSE PLANT NAMED 'WEKMEREADOIT'

(50) Latin Name: *Rosa hybrida*
Varietal Denomination: WEKmereadoit

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 15/732,476

(22) Filed: Nov. 16, 2017

(51) Int. Cl.
*A01H 5/02* (2018.01)

(52) U.S. Cl.
USPC ..... Plt./144

(58) Field of Classification Search
USPC ..... Plt./101, 141, 144
See application file for complete search history.

(56) References Cited

U.S. PATENT DOCUMENTS

PP10,126 P 11/1997 Carruth

*Primary Examiner* — Susan McCormick Ewoldt
(74) *Attorney, Agent, or Firm* — McKee, Voorhees & Sease, PLC

(57) ABSTRACT

A new variety of Floribunda rose suitable for garden decoration, having flowers of white with cream base coloration.

1 Drawing Sheet

Classification: The present invention relates to a new *Rosa hybrida* plant.

Variety denomination: The new plant has the varietal denomination 'WEKmereadoit'.

BACKGROUND OF THE INVENTION

This invention relates to a new and distinct variety of Floribunda Rose. It has as its seed parent the variety known as 'WEKmeredoc' (not patented) and as its pollen parent the variety known as 'HARpageant' (U.S. Plant Pat. No. 22,587).

SUMMARY OF THE INVENTION

Among the features which distinguish the new variety from other presently available and commercial rose cultivars known to the inventor are the following combinations of characteristics: its elegant white with cream base high centered flowers, its high degree of resistance to powdery mildew, downy mildew and rust, its excellent color stability throughout the life of the flowers and its abundant blooms. The plant has an upright slightly spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKmereadoit' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKmeredoc' by the following combination of characteristics: whereas 'WEKmereadoit' bears very double flowers (about 29 to 53 petals) of white with cream base coloration, 'WEKmeredoc' bears double flowers of light pink with darker undertones coloration with significantly lesser petalage (about 17 to 25 petals). The new variety has an upright slightly spreading medium height growing habit (about 90 to about 150 cm. in height), whereas the seed parent has an upright bushy significantly shorter growing habit (about 90 cm. in height).

The new variety may be distinguished from its pollen parent, 'HARpageant' by the following combination of characteristics: whereas 'WEKmereadoit' bears very double flowers (about 29 to 53 petals) of white with cream base coloration, 'HARpageant' bears double flowers of mango, peach & apricot blend coloration with significantly lesser petalage (about 20 to 32 petals). The new variety bears medium to large sized flowers (about 7.9 to about 13.4 cm. in diameter), whereas the pollen parent bears smaller flowers (about 7.0 to about 10.6 cm. in diameter).

COMPARISON WITH THE CLOSEST COMMERCIALLY AVAILABLE CULTIVAR

The new variety may be distinguished from its closest commercially available cultivar, 'WEKdidusinra' (U.S. Plant Pat. No. 22,540) by the following combination of characteristics: whereas 'WEKmereadoit' bears very double flowers (about 29 to 53 petals) of white with cream base coloration, 'WEKdidusinra' bears very double flowers of lemon cream coloration with heavier petalage (about 33 to 70 petals). The new variety has a slight tea to moderate fruity fragrance, whereas the closest commercially available cultivar has a strong licorice fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in regular rounded clusters on strong somewhat short to medium length stems (about 20 to about 75 cm.). The cluster ranges from about 20 to about 24 cm. in diameter. Outdoors, the plant blooms abundantly and nearly continuously during the growing season. The flowers have a slight tea to moderate fruity fragrance.

BUD

The peduncle is about 2.7 to about 8.6 cm. in length, of average to somewhat heavy caliper (about 0.2 to about 0.4 cm. in diameter), and usually erect. It is moderately rough, with some stipitate glands, and very few hairs. Peduncle color is between 146C and 146B.

Before the calyx breaks, the bud is about 1.3 to about 1.8 cm. in diameter at the widest point, about 1.7 to about 2.7 cm. in length, and pointed to somewhat ovoid in shape. The surface of the bud bears between 0 to 13 foliaceous appendages with some stipitate glands and hairs, usually with slender entire to sometimes stout much cut foliaceous parts extending beyond the tip of the bud about ½ or more of its length. Bud color is between 137C and 146A sometimes lightly suffused, especially on the side exposed to the sun, with between 187B and 187C.

The sepals are 5 per flower, about 2.1 to about 5.3 cm. in length and about 0.9 to about 1.2 cm. in width at the widest point. The outer surface color of the sepal is between 137C and 146A sometimes lightly suffused, especially on the side exposed to the sun, with between 187B and 187C. The outer surface of the sepal is somewhat rough and bears between 0 to 6 foliaceous appendages with some stipitate glands and hairs. The inner surface color of the sepal is near 146C broadly bordered by near 137A. After the sepals open, the inner surface color is often heavily suffused, especially on the area exposed to the sun, with between 187A and 187B. The inner surface of the sepal is covered with fine wooly tomentum; sepal margins are entire and lined with some stipitate glands and hairs. The sepals are moderately permanent, usually straight in shape with acute apices.

The receptacle of the flower is of moderately short length (about 0.3 to about 0.7 cm.) and somewhat thin to average in caliper (about 0.7 to about 1.0 cm. in diameter). The receptacle is moderately urn-shaped to somewhat rounded in form. Its surface is very smooth with somewhat thin fleshy walls. The receptacle color is between 144A and 146A.

As the petals open (after the calyx breaks), the bud is about 2.3 to about 2.7 cm. in diameter at the widest point, about 2.9 to about 3.9 cm. in length, and moderately ovoid to somewhat pointed in form. The color of the under surfaces of the newly opened petals is between 27A and 8D sometimes lightly suffused with near 59D. At the point where the petal attaches, there is a somewhat large zone of between 154C and 1C. The color of the upper surfaces of the newly opened petals is between 18C and 8D. At the point where the petal attaches, there is a somewhat large zone of between 3C and 4B.

BLOOM

When fully open, the bloom ranges from about 7.9 to about 13.4 cm. in diameter. Petalage is very double with about 29 to 53 petals and about 2 to 10 petaloids irregularly arranged. When partially open, the bloom form is high centered to cupped, and the petals are moderately tightly spiraled to slightly cupped to somewhat undulated with petal edges somewhat reflexed outward. When fully open, the bloom form is moderately high centered to more cupped, and the petals are loosely cupped to somewhat undulated with petal edges moderately reflexed outward.

PETALS

The substance of the petals is somewhat heavy and of moderately thin thickness, with upper surfaces moderately satiny and under surfaces slightly shiny. The petals are about 3.8 to about 5.8 cm. in length and about 3.2 to about 6.2 cm. in width at the widest point. Petal margins are entire.

The outer petals are rounded to somewhat obovate in shape with rounded apices.

The inner petals are moderately obovate in shape with rounded apices and sometimes slightly notched with one notch.

Petaloids are about 1.6 to about 4.1 cm. in length and about 0.9 to about 2.7 cm. in width at the widest point. Petaloids are irregularly shaped moderately obovate to somewhat subulate with rounded apices.

NEWLY OPENED FLOWER

The under and upper surface color of the outer petals is between 155D and 155B. At the point where the petal attaches, there is a small zone of between 4C and 3D.

The under and upper surface color of the intermediate and inner petals is between 11D and 158B.

The under and upper surface colors of the petaloids are similar in coloration to the upper and under surfaces of the intermediate and inner petals.

The general tonality of the newly opened flower is between 11D and 158B.

THREE-DAY-OLD FLOWER

The under and upper surface color of the outer, intermediate and inner petals is between 155D and 155B. At the point where the petal attaches, there is a small zone of near 2D.

The under and upper surface colors of the petaloids are similar in coloration to the upper and under surfaces of the intermediate and inner petals.

The general tonality of the three-day-old flower is between 155D and 155B.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 165) and are arranged regularly about the pistils; a few are mixed with petaloids. The filaments are of moderately short to somewhat long length (about 0.3 to about 1.3 cm.) most with anthers. Filaments are between 4C and 5D in color often lightly suffused with near 53D. The anthers are somewhat small for the class and all open approximately at the same time. Anther color when immature is near 20B on the external part and near 11D on the internal part. Anther color at maturity is near 164C on the external part and near 200A on the internal part. Pollen is moderate and between 22B and 23C in color.

FEMALE REPRODUCTIVE ORGANS

Pistils vary in number (average about 160). The styles are moderately even, average to somewhat long in length (about 0.6 to about 0.9 cm.), somewhat thin to average in caliper, and loosely bunched to moderately separated. Stigma color is between 20B and 18A. Style color is between 10D and 8D often heavily suffused with between 53B and 53C. Ovaries are usually all enclosed in the calyx. The ovaries are of medium size and between 158B and 158C in color.

Hips have not been observed on this variety when grown in Pomona, Calif.

FOLIAGE

The compound leaves are usually comprised of three to seven leaflets and are borne abundantly. The five-leaflet leaves are about 8.8 to about 15.9 cm. in length and about 7.6 to about 11.7 cm. in width at the widest point, moderately leathery to somewhat crisp in texture on both sides, and glossy in finish on the upper side and slightly glossy to matte in finish on the under side. The leaves have a pinnate venation pattern. The terminal leaflets are about 4.7 to about 7.3 cm. in length and about 2.9 to about 5.8 cm. in width at the widest point, shaped ovate with acute apices and rounded to somewhat cordate bases. Their margins are usually simply serrate.

The upper surface color of the mature leaf is between 139A and 137A. The under surface color of the mature leaf is between 147B and 146A. The under and upper colors of the leaf veins on the mature leaf are similar in coloration to the upper and under surfaces colors of the mature leaf. The upper surface color of the young leaf is between 138A and 146B, often moderately suffused with between 187B and 187C. The under surface color of the young leaf is near 146B, often moderately suffused with between 187B and 187C. The under and upper colors of the leaf veins on the young leaf are similar in coloration to the upper and under surfaces colors of the young leaf.

The rachis is about 3.5 to about 8.2 cm. in length, about 0.1 to about 0.2 cm in width at the widest point and rough. The upper side is shallowly grooved with many hairs and few stipitate glands on the edges of the grooves. The under side of the rachis is rough with many hairs, some stipitate glands and few small prickles. The rachis color is near 146D on the under side and near 137C on the upper side, often lightly suffused on the young leaves with between 187B and 187C.

The stipules are about 0.9 to about 1.5 cm. in length and moderately wide (about 0.5 to about 0.9 cm.) with somewhat long straight points that usually turn out at an angle of more than 45 degrees and sometimes recurve toward the stem. The under and upper surface color of the stipule is between 139A and 137A. The upper and under surfaces of the stipules are smooth in texture.

The petiole is moderately heavy in caliper and rough. The upper side is shallowly grooved with many hairs and few stipitate glands on the edges of the grooves. The under side of the petiole is rough with many hairs, some stipitate glands and few small prickles. The petiole is about 0.6 to about 2.2 cm. in length and about 0.1 to about 0.2 cm in width at the widest point. The petiole color is near 146D on the underside and near 137C on the upper side, often lightly suffused on the young leaves with between 187B and 187C.

The plant displays an above average degree of resistance to powdery mildew (*Sphaerotheca pannosa*), downy mildew (*Peronospora sparsa*), black spot (*Diplocarpon rosae*) and rust (*Phragmidium* sp.) as compared to other commercial varieties grown under comparable conditions in Pomona, Calif. The plant's winter hardiness and drought/heat tolerance arc yet to be determined.

GROWTH

The plant has an upright slightly spreading medium height growing habit (about 90 to about 150 cm. in height and about 90 to about 120 cm. spread at the widest point), with full branching. It displays moderately vigorous growth and the canes are of somewhat light caliper for the class (about 1.4 to about 1.9 cm. in diameter at the widest point).

The color of the major stems is between 146A and 147B. The major stems are rough in texture and they bear some large prickles that are about 0.7 to about 1.1 cm. in length. The large prickles are angled slightly downward with a somewhat short to medium length broad to oval base; prickle color is between 165A and 200D. The major stem bears very few small prickles of similar shape and coloration.

The color of the branches is between 137C and 146B. The branches are rough in texture and they bear few large prickles which are of similar size and shape to the large prickles on the major stems; prickle color is between 177B and 164A. The branches bear very few small prickles of similar shape and coloration.

The color of the new shoots is between 146C and 146B sometimes lightly suffused with between 187B and 187C. The new shoots are rough in texture and they bear few large prickles which are of similar size and shape to the large prickles on the major stems; prickle color is between 145A and 146D often moderately suffused with between 187C and 187D. The shoots bear very few small prickles of similar shape and coloration.

I claim:

1. A new and distinct Floribunda rose plant of the variety substantially as described and illustrated herein.

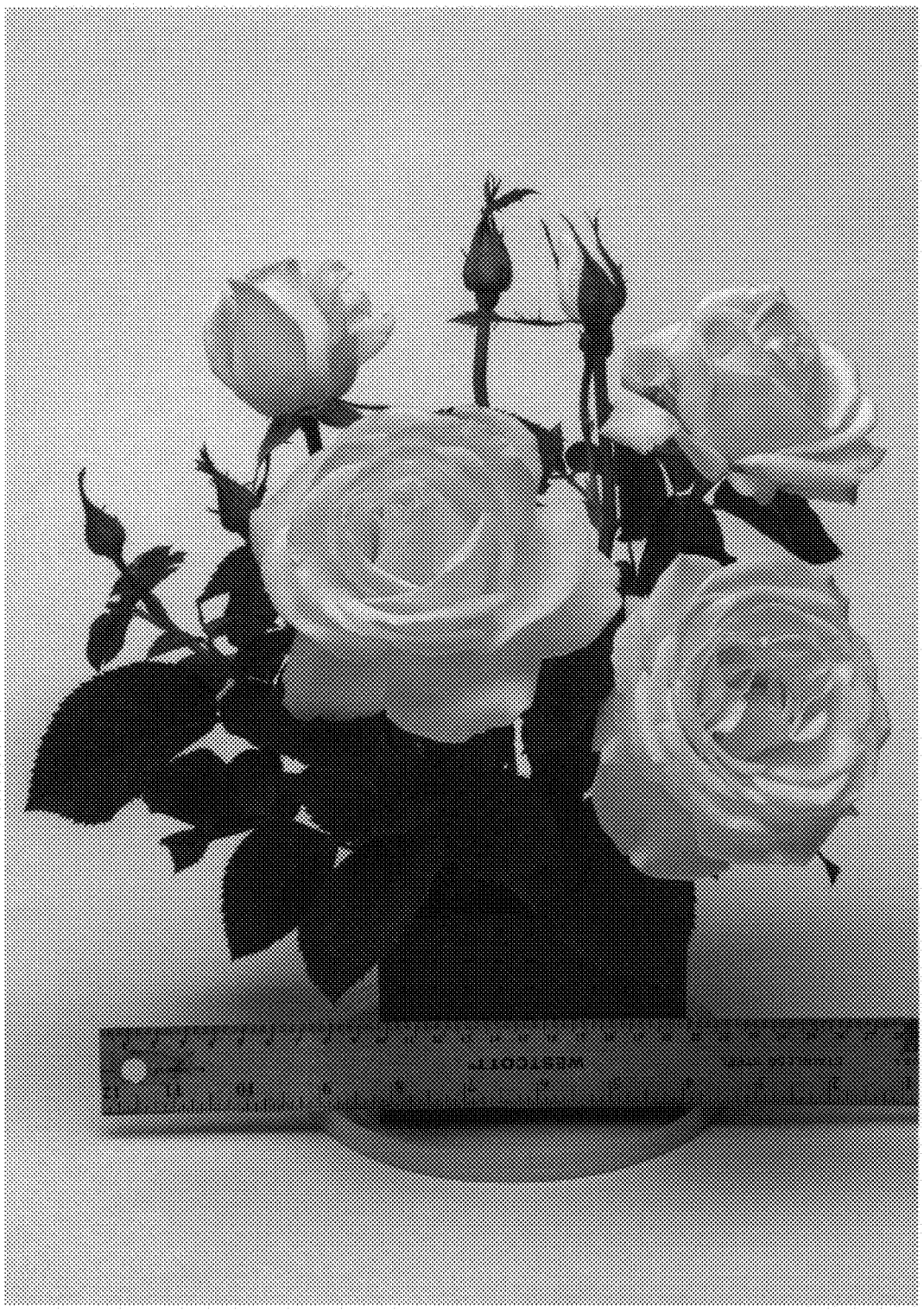

* * * * *